United States Patent [19]
Nohira et al.

[11] Patent Number: 6,069,270
[45] Date of Patent: May 30, 2000

[54] OPTICAL RESOLUTION METHOD OF (±)-3,4-DIHYDROXYBUTANOIC ACID

[75] Inventors: Hiroyuki Nohira; Hiroaki Shitara; Satsuki Inagaki, all of Urawa, Japan

[73] Assignee: Kuraray Co., Ltd., Kurashiki, Japan

[21] Appl. No.: 08/972,145

[22] Filed: Nov. 17, 1997

[30] Foreign Application Priority Data

Nov. 20, 1996 [JP] Japan ................... 8-309208

[51] Int. Cl.⁷ .................... C07B 57/00; C07D 307/32
[52] U.S. Cl. .................................. 562/401; 549/313
[58] Field of Search ................. 562/401; 549/313

[56] References Cited

U.S. PATENT DOCUMENTS

| | | | |
|---|---|---|---|
| 4,845,272 | 7/1989 | Nohira et al. | 562/401 |
| 4,904,822 | 2/1990 | Nohira et al. | |
| 5,191,112 | 3/1993 | Nohira et al. | 562/401 |
| 5,321,154 | 6/1994 | Nohira | 562/401 |
| 5,371,282 | 12/1994 | Nohira et al. | |
| 5,780,649 | 7/1998 | Yuasa et al. | 549/313 |

FOREIGN PATENT DOCUMENTS

| | | |
|---|---|---|
| 4-149152 | 5/1992 | Japan . |
| 4-338359 | 11/1992 | Japan . |
| 6-172256 | 6/1994 | Japan . |
| WO 94/05639 | 3/1994 | WIPO . |

OTHER PUBLICATIONS

E.E. Kim, et al., J. Am. Chem. Soc., vol. 117, pp. 1181 & 1182, 1995, "Crystal Structure of HIV–1 Protease in Complex with VX–478, A Potent and Orally Bioavailable Inhibitor of the Enzyme" Feb. 1995.

J.W.E. Glattfeld, et al., J. Am. Chem. Soc., vol. 42, pp. 2314–2321, 1920, "The $C_4$–Saccharinic Acids. I. The Resolution of DL–2,3–Dioxybutyric Acid into the Optically–Active Components. The Derivatives of These Acids" Apr. 1920.

Optical Resolution Information Center, vol. 2, pp. 83 & 1123, "Optical Resolution Procedures for Chemical Compounds" Aug. 1977.

J.W.E. Glattfeld, "The $C_4$_Saccharinic Acids. I. The resolution of Di–2,3–Diosybutyric Acid Into The Optically–Active Components. The Derivatives of these acids", Journal of the American Chemical Society, vol. 42, No. 11, pp. 2314–2321, Nov. 1920.

J.Jacques et al. "Enantiomers, Racemates and Resolution", Krieger Publishing Company, pp. 253–259 (1991) Month Unavailable.

*Primary Examiner*—Samuel Barts
*Attorney, Agent, or Firm*—Oblon, Spivak, McClelland, Maier & Neustadt, P.C.

[57] ABSTRACT

An optical resolution method of (±)-3,4-dihydroxybutanoic acid, by reacting (±)-3,4-dihydroxybutanoic acid with an optically active primary amine or secondary amine. Also a method for producing optically active 3-hydroxy-γ-butyrolactone, by reacting (±)-3,4-dihydroxybutanoic acid with an optically active primary amine or secondary amine for optical resolution, and ring closing the resulting optically active 3,4-dihydroxybutanoic acid.

8 Claims, No Drawings

OPTICAL RESOLUTION METHOD OF (±)-3, 4-DIHYDROXYBUTANOIC ACID

BACKGROUND OF THE INVENTION

1. Field of the Invention

The present invention relates to an optical resolution method of (±)-3,4-dihydroxybutanoic acid and to a method for producing optically active 3-hydroxy-γ-butyrolactone using optically active 3,4-dihydroxybutanoic acid preferably produced by the aforementioned optical resolution method. Optically active 3-hydroxy-γ-butyrolactone produced by the present invention can readily be introduced into various optically active substances useful as raw materials for the synthesis of pharmaceutical agents, such as optically active 3-hydroxytetrahydrofuran, optically active 4-hydroxypyrrolidinone, optically active 3-hydroxypyrrolidine and optically active 1-amino-2,3-dihydroxypropane, and is a compound of importance as a chiral synthon. For example, optically active 3-hydroxytetrahydrofuran obtained by reducing optically active 3-hydroxy-γ-butyrolactone is useful as a raw material for the synthesis of an HIV protease inhibitor, VX-478 (see J. Am. Chem. Soc., Vol. 117, page 1181 (1995) and WO 94/05639 both incorporated herein by reference).

2. Discussion of the Related Art

The following methods for producing optically active 3,4-dihydroxybutanoic acid are known: (1) a method comprising oxidizing an optically active glucose source (Japanese Patent Laid-open No. Hei 4-338359); (2) a method comprising reducing optically active malic acid derivatives (Japanese Patent Laid-open Nos. Hei 4-149152 and Hei 6-172256); and (3) a method comprising optically resolving (±)-3,4-dihydroxybutanoic acid using brucine (see J. Am. Chem. Soc., Vol. 42, page 2314 (1920) and Optical Resolution Procedures for Chemical Compounds, Vol. 2, Acids Part I, page 83 (Optical Resolution Information Center)).

However, method (1) requires the removal of by-product glycolic acid, generated together with optically active 3,4-dihydroxybutanoic acid, by silica gel chromatography. With method (2), optically active malic acid (raw material) and sodium borohydride (reducing agent) are expensive. Method (3) uses brucine (an alkaloid) as a resolving agent, which is hardly available at low cost, and therefore, the method is not suitable as an industrial process.

Hence, a method for optically resolving the raw material (±)-3,4-dihydroxybutanoic acid with a readily available resolving agent at low cost is currently in demand.

SUMMARY OF THE INVENTION

It is an object of the present invention to provide a method for optically resolving (±)-3,4-dihydroxybutanoic acid with a readily available resolving agent at low cost.

It is another object of the present invention to provide a method for producing optically active 3-hydroxy-γ-butyrolactone, preferably comprising optically resolving the raw material (±)-3,4-dihydroxybutanoic acid with a readily available resolving agent at low cost, comprising ring closing optically active 3,4-dihydroxybutanoic acid.

More specifically, the first aspect of the present invention is to provide a method for optically resolving (±)-3,4-dihydroxybutanoic acid, comprising reacting (±)-3,4-dihydroxybutanoic acid with an optically active primary amine or secondary amine.

Additionally, the second aspect of the present invention is to provide a method for producing optically active 3-hydroxy-γ-butyrolactone, preferably comprising optically resolving (±)-3,4-dihydroxybutanoic acid by reacting (±)-3,4-dihydroxybutanoic acid with an optically active primary amine or secondary amine, and comprising ring closing (the resulting) optically active 3,4-dihydroxybutanoic acid.

DETAILED DESCRIPTION OF THE INVENTION

The optical resolution method of the present invention requires the use of an optically active primary amine or secondary amine as a resolving agent. Mixtures may be used but are not preferred. More specifically, use is made of optically active 1-(p-tolyl)ethylamine, optically active erythro-2-amino-1,2-diphenylethanol, optically active 1-(p-isopropylphenyl)ethylamine, optically active 1-ethylbenzylamine, optically active N-(2-hydroxy)ethyl-α-methylbenzylamine, optically active 1-(1-naphthyl)ethylamine, optically active 1-phenyl-2-(p-tolyl)ethylamine, and optically active 2-phenyl-3-methyl-2-butylamine. Among them, preference is given to optically active 1-(p-tolyl)ethylamine and optically active erythro-2-amino-1,2-diphenylethanol. An optically active primary amine or secondary amine is used at any amount, with no specific limitation, but preferably the amine is used within a range of 0.4 to 1 equivalent of (±)-3,4-dihydroxybutanoic acid, to encourage resolution at high efficiency and high purity.

By the action of such resolving agent, diastereomer salts corresponding to (+)-3,4-dihydroxybutanoic acid and (−)-3,4-dihydroxybutanoic acid are formed. When (+)-1-(p-tolyl)ethylamine is used as a resolving agent, for example, (+)-3,4-dihydroxybutanoic acid·(+)-1-(p-tolyl)ethylamine salt and (−)-3,4-dihydroxybutanoic acid·(+)-1-(p-tolyl)ethylamine salt are formed. When (−)-erythro-2-amino-1,2-diphenylethanol is used as a resolving agent, for example, (+)-3,4-dihydroxybutanoic acid·(−)-erythro-2-amino-1,2-diphenylethanol salt and (−)-3,4-dihydroxybutanoic acid·(−)-erythro-2-amino-1,2-diphenylethanol salt are formed. These diastereomer salts may be formed by reacting a salt of an optically active amine with a salt of (±)-3,4-dihydroxybutanoic acid, for example, produced by hydrolyzing (±)-3-hydroxy-γ-butyrolactone with a base. By separating these diastereomer salts utilizing their difference in solubility in solvent, racemic (±)-3,4-dihydroxybutanoic acid can be optically resolved into (+)-3,4-dihydroxybutanoic acid and (−)-3,4-dihydroxybutanoic acid.

The separating solvent to be herein used preferably includes for example alcohols such as methanol, ethanol, 2-propanol, and 1-propanol; ketones such as acetone and methyl isobutyl ketone; esters such as ethyl acetate and butyl acetate; aromatic hydrocarbons such as benzene, toluene, and xylene; aliphatic hydrocarbons such as n-hexane, n-heptane, and cyclohexane; ethers such as diethyl ether, diisopropyl ether, dioxane, tetrahydrofuran, tetrahydropyran, and t-butyl methyl ether; water; or a mixture thereof. Among them, preference is given to water, ethanol, 2-propanol, acetone, ethyl acetate, diisopropyl ether, t-butyl methyl ether or a mixture solvent thereof, from the point of view of recovery of optically active 3,4-dihydroxybutanoic acid at a high purity.

The amount of the solvent to be used varies depending on the solvent type, the solubility of the salts and the crystallization temperature, and is within the skill of the ordinary artisan. The solvent is generally used within a range of 150 to 1500 ml per one mole of an optically active primary amine or secondary amine. The crystallization temperature is appropriately selected, depending on the amount and type of a solvent to be used and the dissolution temperature thereof, but from economical standpoint, preferably, the temperature is within a range of −10° to 50° C.

The optical resolution method of the present invention is carried out for example as follows. (±)-3,4-Dihydroxybutanoic acid is dissolved or suspended in an appropriate solvent, to which is added an optically active primary amine or secondary amine dissolved in an appropriate solvent, followed by dissolution under heating, and the resulting solution is cooled to a supersaturated state. To the resulting solution is seeded, optionally, a small amount of a diastereomer salt of the same optically active primary amine or secondary amine as used as the raw material [(+)-3,4-dihydroxybutanoic acid·(−)-1-(p-tolyl)ethylamine salt, (−)-3,4-dihydroxybutanoic acid·(+)-1-(p-tolyl)ethylamine salt, (+)-3,4-dihydroxybutanoic acid (+)-erythro-2-amino-1,2-diphenylethanol salt, (−)-3,4-dihydroxybutanoic acid·(−)-erythro-2-amino-1,2-diphenylethanol salt and the like], to deposit the same diastereomer salt, which is then isolated.

As the method for isolating the diastereomer salt thus recovered, use is made of methods such as filtration and centrifugation. The resulting diastereomer salt is purified by using an appropriate solvent, followed by treatment with bases such as sodium hydroxide, potassium hydroxide, and sodium methoxide, to recover the optically active primary amine or secondary amine used as the resolving agent. Then, (+)-3,4-dihydroxybutanoic acid or (−)-3,4-dihydroxybutanoic acid is recovered through the action of acids such as hydrochloric acid, sulfuric acid, phosphoric acid and p-toluenesulfonic acid. Furthermore, the above procedures may satisfactorily be carried out by acid treatment and subsequent optional base treatment in this order.

The optically active 3,4-dihydroxybutanoic acid thus recovered may be converted into 3-hydroxy-γ-butyrolactone by ring closing reactions according to methods known to those or ordinary skill.

The (±)-3,4-dihydroxybutanoic acid raw material of the present invention can be produced by reacting 3-chloro-1,2-propanediol with sodium cyanide and potassium cyanide to produce 3,4-dihydroxybutyronitrile, followed by hydrolysis. Thus, the afforded (±)-3,4-dihydroxybutanoic acid is further subjected to cyclization, to produce (±)-3-hydroxy-γ-butyrolactone, followed by the action of bases such as aqueous sodium hydroxide solution for opening the lactone ring to afford the salt of (±)-3,4-dihydroxybutanoic acid.

EXAMPLES

The present invention will now be further described by the following examples, but the invention is not limited to these examples.

In the following examples 3,4-dihydroxybutanoic acid is abbreviated as DHB; 1-(p-tolyl)ethylamine is abbreviated as TEA; and erythro-2-amino-1,2-diphenylethanol is abbreviated as ADPE.

Example 1

(±)-DHB (615 mg; 5.12 mmol) recovered through the reaction of (±)-3-dihydroxy-γ-butyrolactone with an aqueous sodium hydroxide solution was dissolved in acetone (7 ml), followed by dropwise addition of (+)-TEA (659 mg; 4.87 mmol) dissolved in acetone (3 ml) under agitation. After the addition, the resulting mixture was left to stand at room temperature for 3 hours, and then, the deposited white crystal was filtered, to recover (−)-DHB·(+)-TEA salt (286 mg; 1.12 mmol). The yield of the (−)-DHB based on the (±)-DHB used was 43.8%; and the melting point was 128 to 130.5° C.

2-Propanol (0.7 ml) was added to the resulting (−)-DHB·(+)-TEA salt (282 mg; 1.11 mmol) to dissolve the salt under heating, followed by addition of acetone (1 ml) to leave the resulting mixture to stand overnight at room temperature. The deposited crystal was filtered, to recover (−)-DHB·(+)-TEA salt (187 mg; 0.733 mmol) in white crystal. The melting point was 138.5 to 141.5° C. After recovering the (+)-TEA by treating the product with sodium hydroxide solution, followed by lactonization of resulting (−)-DHB with hydrochloric acid, (S)-(−)-3-hydroxy-γ-butyrolactone was recovered. The specific rotation was $[\alpha]^{31}_D = -54.0°$ (c 0.5, ethanol). Furthermore, the (S)-(−)-3-hydroxy-γ-butyrolactone was benzoylated by benzoyl chloride, followed by purification by silica gel chromatography and assaying of the optical purity by HPLC. The optical purity was 71.4% ee.

HPLC conditions;
column: CHIRALPAK AD (manufactured by Daicel Chemical Industry)
mobile phase: 2-propanol/n-hexane (1:9)
flow rate: 0.5 ml/min
detection wave length: 254 nm.

Example 2

Example 2-1

(+)-TEA (1220 mg; 9.02 mmol) was suspended in water (10 ml), and to the resulting suspension was dropwise added (±)-DHB (1233 mg; 10.27 mmol) dissolved in water (10 ml). After the addition, the suspension was stirred at room temperature for 18 hours and at 50° C. for 8 hours. The aqueous solution was concentrated under reduced pressure, followed by addition of ethanol (5 ml) and subsequent addition of benzene (5 ml) for repeating concentration, to recover a concentrated solution of (±)-DHB·(+)-TEA salt (2636 mg).

Example 2-2

To 874 mg of the concentrated solution recovered in Example 2-1 was added with the seed crystal of (−)-DHB·(+)-TEA salt followed by rubbing, so that the solution was solidified and turned into pale yellow crystal. To the crystal was added a mixture solvent of ethanol and ethyl acetate (1:1; 3 ml) to heat the mixture to 70° C., thereby solubilizing a part thereof, which was then left to stand overnight. The deposited crystal was filtered to recover (−)-DHB·(+)-TEA salt (381 mg; 1.49 mmol) in white crystal. The yield of the resulting (−)-DHB based on the (±)-DHB was 82.7%, and the melting point thereof was 137 to 144° C.

To the resulting (−)-DHB·(+)-TEA salt (377 mg; 1.48 mmol) was added ethanol (1.6 ml), under heating for dissolution, and to the resulting mixture was added ethyl acetate (1.6 ml) to leave the solution overnight at room temperature. The resulting crystal was filtered, to recover (−)-DHB·(+)-TEA salt (274 mg; 1.07 mmol) in white crystal. The yield of the resulting (−)-DHB based on the (±)-DHB was 59.6%; the specific rotation of the salt was $[\alpha]^{31}_D = -2.1°$ (c 1.0, ethanol); and the melting point thereof was 142 to 147° C. After decomposing a part of the salt, followed by lactonation with hydrochloric acid, (S)-(−)-3-hydroxy-γ-butyrolactone was recovered. The specific rotation was $[\alpha]^{31}_D = -67.7°$ (c 0.3, ethanol). Additionally, the purity was assayed by HPLC. The optical purity was 87.2% ee.

Furthermore, ethanol (1.5 ml) was added to the (−)-DHB·(+)-TEA salt (157 mg; 0.615 mmol) to heat the resulting mixture to 70° C. for completely dissolving the salt, followed by addition of ethyl acetate (1.5 ml), and the resulting solution was left to stand overnight. The resulting white crystal was filtered, to recover purified (−)-DHB·(+)-TEA salt (114 mg; 0.446 mmol). The specific rotation of the salt was $[\alpha]^{31}_D=-3.2°$ (c 0.9, ethanol). The melting point was 147 to 148° C. After decomposing the product, followed by lactonation with hydrochloric acid, (S)-(−)-3-hydroxy-γ-butyrolactone was recovered. The specific rotation was $[\alpha]^{31}_D=-67.9°$ (c 0.3, ethanol). As the result of the purity assay by HPLC, the optical purity was 96.7% ee. The resolving efficiency was 41.7%.

Example 2-3

To 867 mg of the concentrated solution of (±)-DHB·(+)-TEA salt as recovered in Example 2-1 was added ethanol (2.2 ml), prior to dissolution under heating. To the resulting solution was added t-butyl methyl ether (2.2 ml), and the resulting mixture was left to stand at room temperature overnight. The deposited crystal was filtered, to recover (−)-DHB·(+)-TEA salt (333 mg; 1.31 mmol) in white crystal. The yield of the resulting (−)-DHB based on the (±)-DHB was 70.6%, and the melting point thereof was 139 to 145° C.

To the resulting (−)-DHB·(+)-TEA salt (333 mg; 1.31 mmol) was added ethanol (1.7 ml), under heating for dissolution, and to the resulting mixture was added t-butyl methyl ether (1.7 ml), to leave the solution overnight at room temperature. The resulting crystal was filtered, to recover (−)-DHB·(+)-TEA salt (256 mg; 1.01 mmol) in white crystal. The yield of the resulting (−)-DHB based on the (±)-DHB used was 54.2%; and the melting point thereof was 145 to 146° C.

Furthermore, ethanol (2.5 ml) was added to the (−)-DHB·(+)-TEA salt (256 mg; 1.01 mmol) to dissolve the resulting mixture under heating, and to the resulting solution was added t-butyl methyl ether (2.5 ml), to leave the solution at room temperature for 4 hours. The resulting crystal was filtered, to recover purified (−)-DHB·(+)-TEA salt (184 mg; 0.72 mmol) in white crystal. The yield of the resulting (−)-DHB based on the (±)-DHB used was 39.0%; and the specific rotation of the salt was $[\alpha]^{27}_D=-3.2°$ (c 1.0, ethanol). The melting point was 147 to 150° C. After decomposing a part of the salt, followed by lactonation with hydrochloric acid, (S)-(−)-3-hydroxy-γ-butyrolactone was recovered. The specific rotation was measured as $[\alpha]^{26}_D=-50.6°$ (c 0.4, ethanol). As the result of the purity assay by HPLC, the optical purity was 99.1% ee. The resolving efficiency was 38.6%.

Example 3

(±)-DHB (12.01 g; 100 mmol) was dissolved in water (200 ml), followed by addition of 1N sodium hydroxide solution (100 ml) and subsequent dropwise addition of a mixture solution of (+)-TEA (13.52 g; 100 mmol), 1N hydrochloric acid (105 ml) and water (200 ml) under cooling with ice bath, and the resulting solution was continuously stirred overnight at room temperature. The aqueous solution was concentrated under reduced pressure, followed by addition of ethanol for repeating concentration (100 ml of ethanol added three times), and to the resulting residue was added ethanol to filter insoluble matters off. Then, the resulting filtrate was concentrated under reduced pressure, to recover (±)-DHB·(+)-TEA salt (31.82 g) in pale brown partially oily crystal.

Furthermore, the recovered (±)-DHB·(+)-TEA salt (26.79 g) was dissolved in ethanol (54 ml) under heating, followed by dropwise addition of diisopropyl ether (107 ml), and the resulting mixture was gradually cooled overnight. Then, the mixture was cooled in ice (3° C. for 2 hours), to filter the deposited crystal and rinse the crystal in ethanol-diisopropyl ether (1:3) (30 ml×3), to recover (−)-DHB·(+)-TEA salt (10.68 g; 41.8 mmol) in white crystal (yield of 79.7%). A part thereof was decomposed in sodium hydroxide solution, followed by lactonation with hydrochloric acid, to recover (S)-(−)3-hydroxy-γ-butyrolactone. Further, the lactone was converted into a benzoyl form, of which the optical purity was assayed by HPLC. The optical purity was 80.6% ee; and the resolving efficiency was 67.4%.

By recrystallizing the recovered (−)-DHB·(+)-TEA salt (10.46 g) by using ethanol (25 ml) and diisopropyl ether (2 ml) following the same procedures as described above, purified (−)-DHB , (+)-TEA salt (8.41 g; 32.9 mmol) was recovered at a yield of 62.8%. This product was (S)-(−)-3-hydroxy-γ-butyrolactone at an optical purity of 96.6% ee, as determined by optical purity analysis by HPLC. Additionally, the resolving efficiency was 60.6%.

Example 4

After pH adjustment to 6 with hydrochloric acid, an aqueous solution of (1R, 2S)-(−)-ADPE (6512 mg; 3.05 mmol) was added to an aqueous sodium salt solution of (±)-DHB, which was preliminarily produced through the reaction of (±)-3-hydroxy-γ-butyrolactone (3641 mg; 3.03 mmol) with an aqueous sodium hydroxide solution, and the resulting mixture was stirred overnight. The water was evaporated, followed by addition of benzene (6 ml) for dehydration. Desalting process with ethanol (10 ml) was repeated three times, to recover (±)-DHB·(−)-ADPE salt (9095 mg).

The resulting (±)-DHB·(−)-ADPE salt was dissolved in ethanol (7 ml) under heating and left to stand as it was, and subsequently, the deposited white crystal was filtered under aspiration, to recover (−)-DHB·(−)-ADPE salt (4695 mg; 1.40 mmol). The yield of the (−)-DHB relative to the (±)-DHB used was 92%; and the melting point was 125 to 131° C.

By solvent evaporation of the mother solution, (+)-DHB·(−)-ADPE salt (4614 mg; 1.38 mmol) was recovered. The yield of the (+)-DHB relative to the (±)-DHB used was 91%. After decomposing the product in sodium hydroxide solution, followed by lactonization with p-toluenesulfonic acid, (R)-(+)-3-hydroxy-γ-butyrolactone was recovered. The specific rotation was as follows; $[\alpha]^{26}_D=+19.1°$ (c 0.68, ethanol); and the optical purity was 22% ee.

Japanese patent application 309208/1996 filed Nov. 20, 1996, is incorporated herein by reference.

What is claimed as new and is desired to be secured by Letters Patent of the United States is:

1. A method for optically resolving (±)-3,4-dihydroxybutanoic acid, comprising reacting (±)-3,4-dihydroxybutanoic acid with optically active 1-(p-tolyl)ethylamine to form diasteriomer salts, separating said diasteriomer salts utilizing their difference in solubility in a solvent, isolating one of said diasteriomer salts, and treating at least one of said separated diasteriomer salts to liberate optically resolved 3,4-dihydroxybutanoic acid.

2. The method according to claim 1, wherein said (±)-3, 4-dihydroxybutanoic acid is produced by hydrolyzing (±)-3-hydroxy-γ-butyrolactone with a base.

3. The method according to claim 1, wherein the amount of said optically active amine reactant ranges from 0.4–1 equivalent of (±)-3,4-dihydroxybutanoxic acid.

4. The method of claim 1, wherein said solvent comprises at least one member selected from the group consisting of water, ethanol, 2-propanol, acetone, ethyl acetate, diisopropyl ether, and t-butylmethyl ether.

5. A method for producing an optically active 3-hydroxy-γ-butyrolactone, comprising reacting (+)-3,4-dihydroxybutanoic acid with optically active 1-(p-tolyl)ethylene to form diasteriomer salts, separating said salts utilizing their difference in solubility in a solvent, isolating at least one of said separated diasteriomer salts, treating said diasteriomer salt to liberate optically resolved 3,4-dihydroxybutanoic acid and ring closing the resulting optically active 3,4-dihydroxybutanoic acid.

6. The method according to claim 5, wherein said salts are separated by separation in a solvent selected from the group consisting of water, ethanol, 2-propanol, acetone, ethylacetate, diisopropyl ether, t-butyl methyl ether and combinations thereof.

7. The method according to claim 6, wherein the amount of solvent employed ranges from 150–1500 ml per mol of optically active 1-(p-tolyl)ethylamine.

8. The method according to claim 6, wherein the temperature of solvent resolution ranges from −10 to 50° C.

* * * * *